(12) United States Patent
Okada

(10) Patent No.: US 9,943,215 B2
(45) Date of Patent: Apr. 17, 2018

(54) ENDOSCOPIC OPERATION PORTION AND ENDOSCOPE

(71) Applicant: OLYMPUS CORPORATION, Hachioji-shi, Tokyo (JP)

(72) Inventor: Takeshi Okada, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/255,954

(22) Filed: Sep. 2, 2016

(65) Prior Publication Data

US 2017/0143190 A1  May 25, 2017

Related U.S. Application Data

(63) Continuation of application No. PCT/JP2015/060225, filed on Mar. 31, 2015.

(30) Foreign Application Priority Data

Apr. 22, 2014 (JP) ................................ 2014-088520

(51) Int. Cl.
*A61B 1/00* (2006.01)
*A61B 1/045* (2006.01)
(Continued)

(52) U.S. Cl.
CPC ...... *A61B 1/00066* (2013.01); *A61B 1/00039* (2013.01); *A61B 1/00112* (2013.01);
(Continued)

(58) Field of Classification Search
CPC . A61B 1/00039; A61B 1/045; A61B 1/00068; A61B 1/00112
(Continued)

(56) References Cited

U.S. PATENT DOCUMENTS 3,932,722 A * 1/1976 Obata .................. H01H 13/702
200/302.2
4,536,625 A * 8/1985 Bebie .................. H01H 13/702
200/339
(Continued)

FOREIGN PATENT DOCUMENTS

JP  2002-306405 A  10/2002
JP  2004-290321 A  10/2004
(Continued)

OTHER PUBLICATIONS

Nov. 3, 2016 International Preliminary Report on Patentability issued in International Application No. PCT/JP2015/060225.
(Continued)

*Primary Examiner* — Matthew J Kasztejna
(74) *Attorney, Agent, or Firm* — Oliff PLC

(57) ABSTRACT

A holder which is disposed inside an endoscopic operation section and which fixes the flexible substrate, includes a first opening to pass the flexible substrate into the holder from the outside of the holder, a cavity portion which has a ceiling portion in the inner circumferential surface thereof and in which the flexible substrate is disposed in a bent state inside the holder, and a second opening to pass the flexible substrate to the outside of the holder from the inside of the holder. The flexible substrate is disposed separately from the ceiling portion of the cavity portion in a state where the flexible substrate protruding to the outside of the holder from the first opening and the second opening is fixed to the outer circumference of the holder.

14 Claims, 13 Drawing Sheets

(51) Int. Cl.
*A61B 1/06* (2006.01)
*G02B 23/24* (2006.01)

(52) U.S. Cl.
CPC ............ *A61B 1/045* (2013.01); *A61B 1/0669* (2013.01); *G02B 23/2461* (2013.01); *G02B 23/2476* (2013.01); *A61B 1/00068* (2013.01)

(58) Field of Classification Search
USPC .................................................. 600/130, 152
See application file for complete search history.

(56) References Cited

U.S. PATENT DOCUMENTS

| | | | | |
|---|---|---|---|---|
| 4,661,005 A | * | 4/1987 | Lahr .......................... | B41J 5/105 340/407.2 |
| 2004/0176660 A1 | * | 9/2004 | Abe .................. | A61B 1/00059 600/101 |
| 2005/0274595 A1 | * | 12/2005 | Pihlaja ................ | H01H 13/702 200/512 |
| 2006/0137966 A1 | * | 6/2006 | Kato .................... | H01H 13/705 200/512 |
| 2008/0275303 A1 | * | 11/2008 | Koitabashi ........... | A61B 1/0052 600/146 |
| 2008/0296141 A1 | * | 12/2008 | Ogatsu ................. | H01H 13/705 200/535 |
| 2010/0000847 A1 | * | 1/2010 | Keist .................... | H01H 13/705 200/341 |
| 2014/0100424 A1 | * | 4/2014 | Hoshino ................ | H01H 13/14 600/118 |

FOREIGN PATENT DOCUMENTS

| | | |
|---|---|---|
| JP | 2006-288614 A | 10/2006 |
| WO | 2013/154106 A1 | 10/2013 |

OTHER PUBLICATIONS

May 26, 2015 International Search Report issued in Patent Application No. PCT/JP2015/060225.

Dec. 15, 2015 Office Action issued in Japanese Patent Application No. 2015-553972.

* cited by examiner

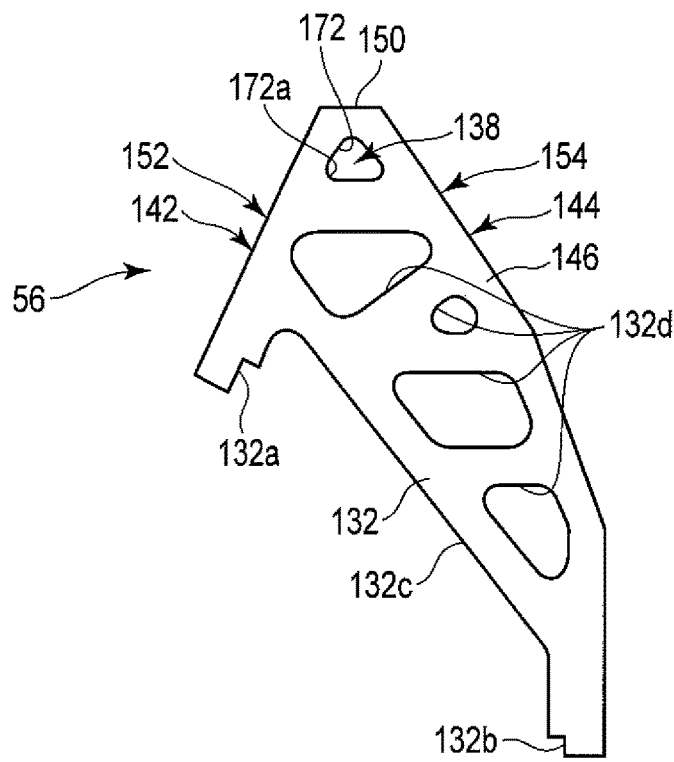
F I G. 6A
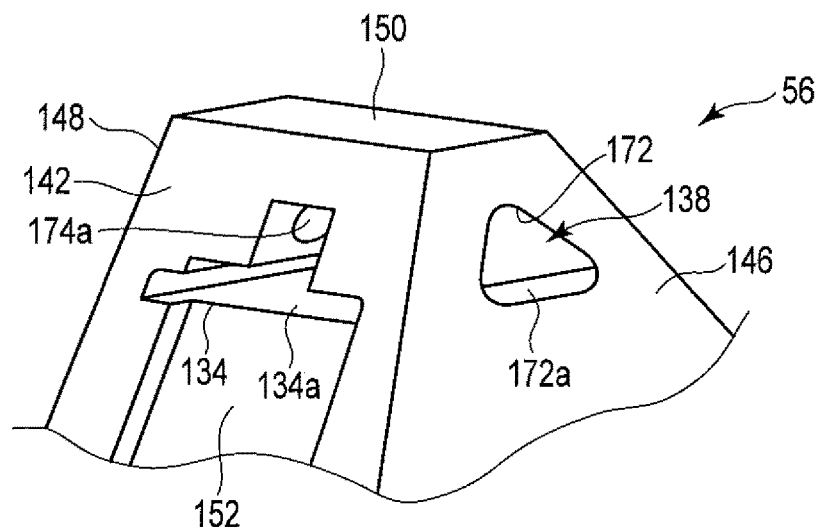
F I G. 6B

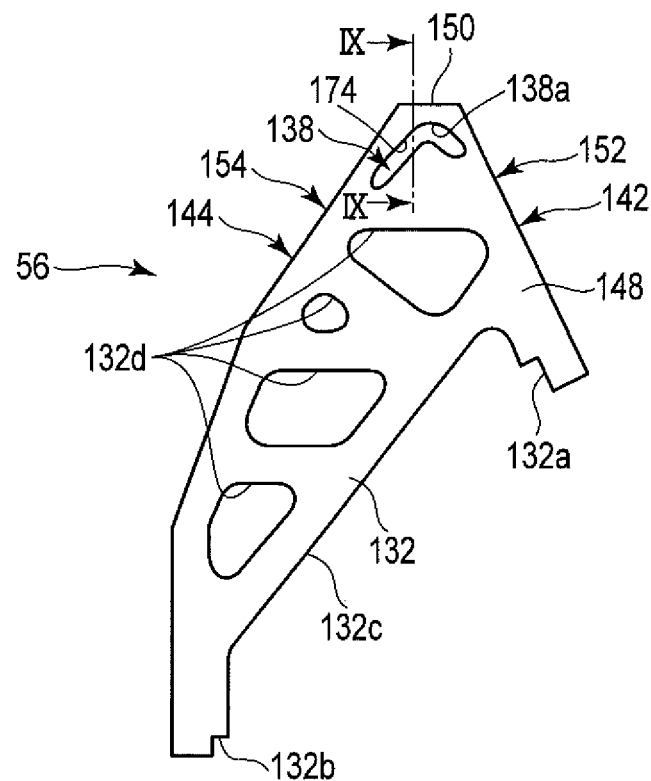
F I G. 7A
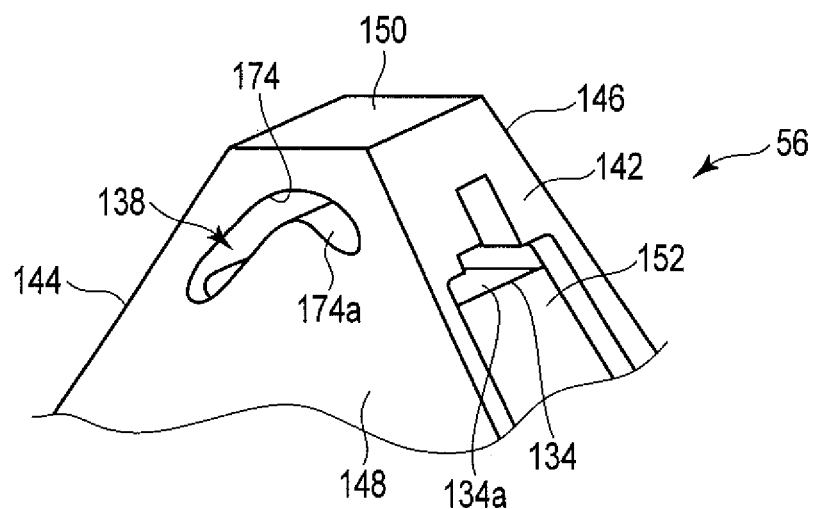
F I G. 7B

ENDOSCOPIC OPERATION PORTION AND ENDOSCOPE

CROSS-REFERENCE TO RELATED APPLICATIONS

This application is a Continuation Application of PCT Application No. PCT/JP2015/060225, filed Mar. 31, 2015 and based upon and claiming the benefit of priority from prior Japanese Patent Application No. 2014-088520, filed Apr. 22, 2014, the entire contents of all of which are incorporated herein by reference.

BACKGROUND OF THE INVENTION

1. Field of the Invention

The present invention relates to an endoscopic operation section and an endoscope.

2 Description of the Related Art

For example, as disclosed in International Publication No. 2013/154106, a flexible substrate having key portions is used in an operation section of an endoscope to suitably operate an illumination optical system and an observation optical system. In a state where the flexible substrate is held to a holder, the holder is attached to an operation section main body.

BRIEF SUMMARY OF THE INVENTION

According to one aspect of the present invention, an endoscopic operation section to operate an endoscope, includes: an elastically deformable belt-shaped flexible substrate which is disposed inside the endoscopic operation section and which has a switch function; and a holder which is disposed inside the endoscopic operation section and which fixes the flexible substrate, the holder including: a first opening to pass the flexible substrate into the holder from the outside of the holder, a cavity portion which has a ceiling portion in the inner circumferential surface thereof and in which the flexible substrate is disposed in a bent state inside the holder, and a second opening to pass the flexible substrate to the outside of the holder from the inside of the holder, wherein the flexible substrate is disposed separately from the ceiling portion of the cavity portion in a state where the flexible substrate protruding to the outside of the holder from the first opening and the second opening is fixed to the outer circumference of the holder.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 6A is a schematic plan view showing the holder provided inside the operation section of the endoscope according to one embodiment;

FIG. 6B is a schematic perspective view showing the vicinity of the top of the holder provided inside the operation section of the endoscope according to one embodiment;

FIG. 7A is a schematic plan view showing a state where the holder provided inside the operation section of the endoscope according to one embodiment is seen from the side opposite to that in FIG. 6A;

FIG. 7B is a schematic perspective view showing the vicinity of the top of the holder provided inside the operation section of the endoscope according to one embodiment;

DETAILED DESCRIPTION OF THE INVENTION

Hereinafter, one embodiment of this invention will be described with reference to the drawings.

Figure 1:
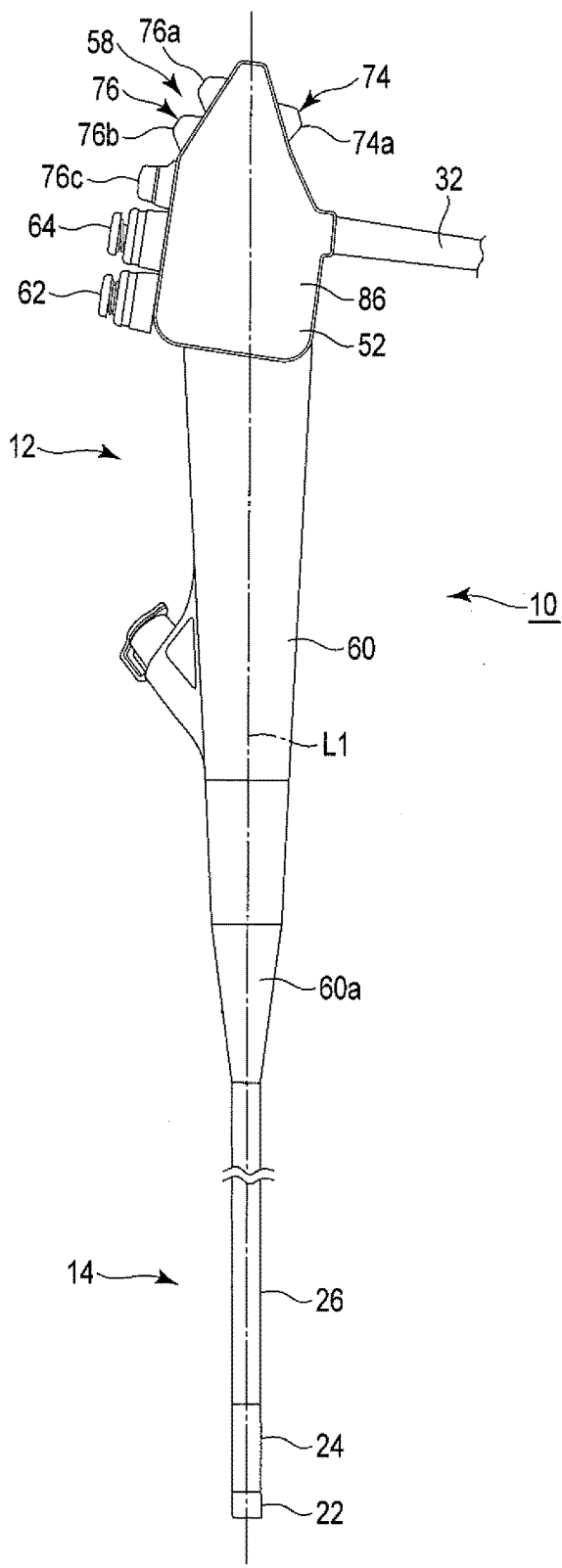
FIG. 1 is a schematic diagram showing an endoscope according to one embodiment.

As shown in FIG. 1, an endoscope 10 includes an operation section 12 to operate the endoscope 10, and an insertion section 14 coupled to the operation section 12. The operation section 12 is provided on the proximal side of the insertion section 14 along a longitudinal direction L1. The insertion section 14 has a distal hard portion 22, a curving portion 24, and a flexible tubular portion 26 from the distal end to the proximal end in order along the longitudinal direction L1. The proximal end of the flexible tubular portion 26 is connected to the operation section 12.

The operation section 12 has a universal cord 32. The universal cord 32 has, at the distal end to a later-described operation section main body 52, a connector 34 which is connected to a controller including a light source device and a camera control unit that are not shown.

Figure 2:
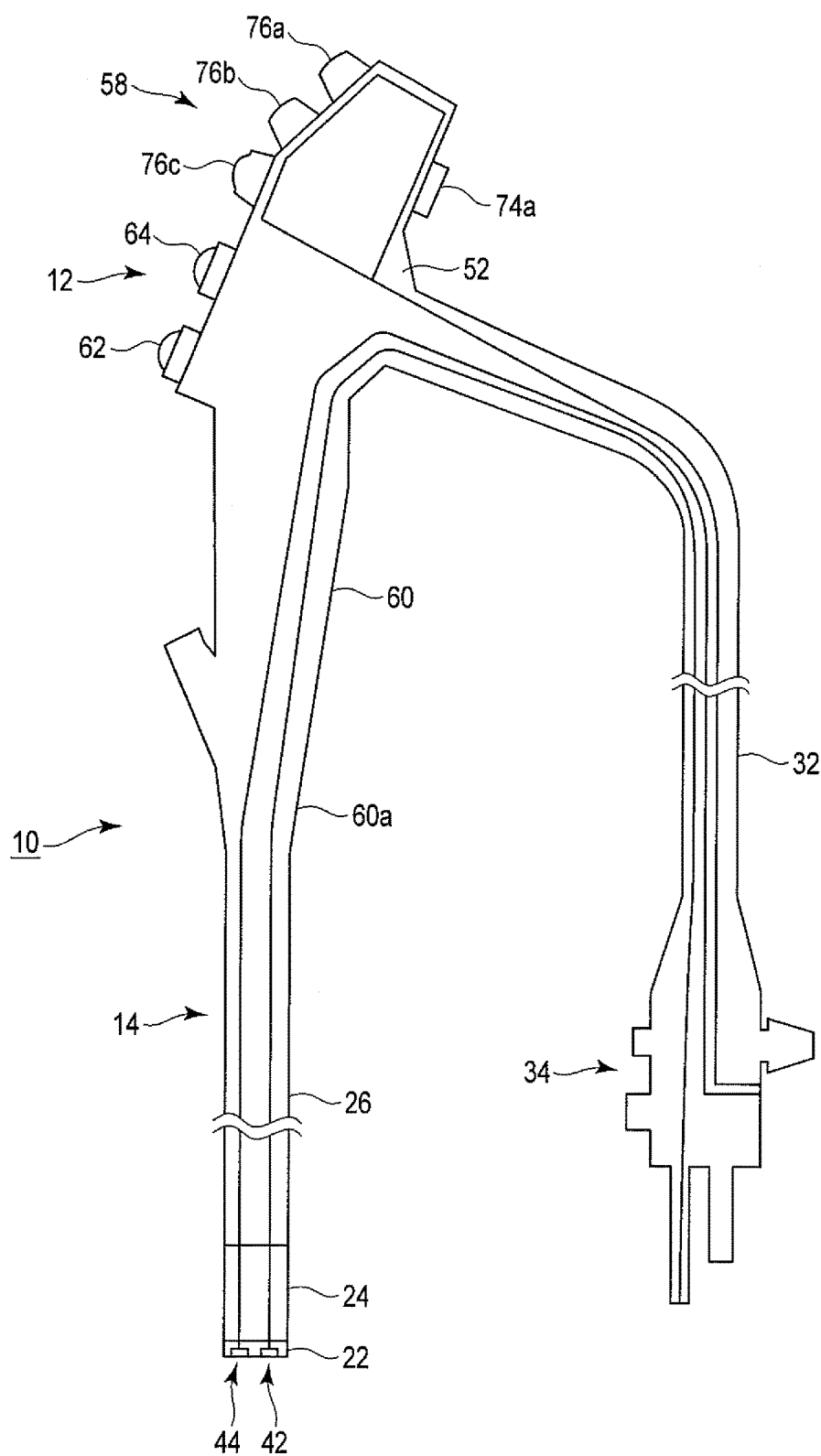
FIG. 2 is a schematic diagram showing the endoscope according to one embodiment.

As shown in FIG. 2, an illumination optical system 42 and an observation optical system 44 are provided in parallel inside the operation section 12 and the insertion section 14 of the endoscope 10. The illumination optical system 42 and the observation optical system 44 are controlled to perform suitable functions when first and second press portions 74 and 76 of a later-described press unit 58 are pressed.

Figure 3:
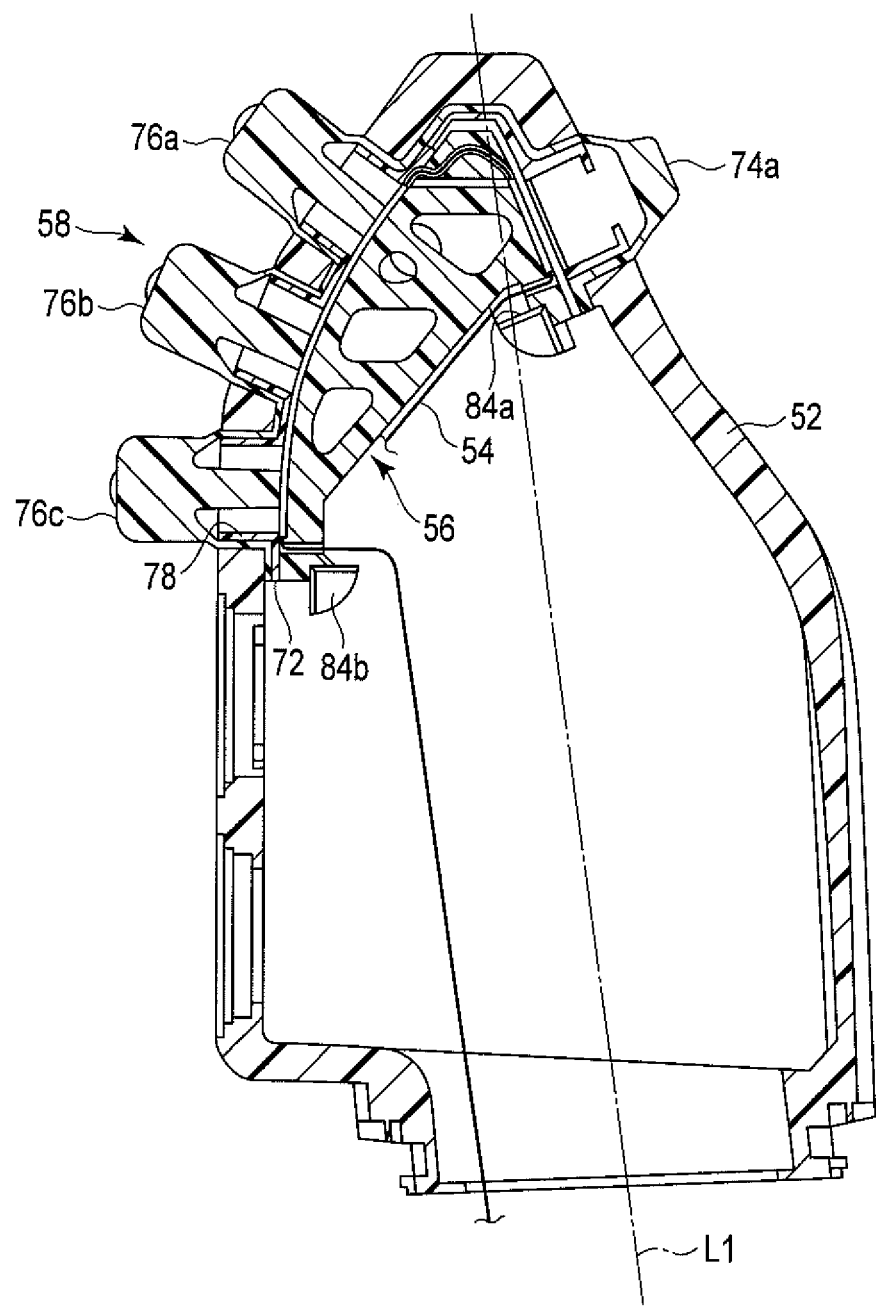
FIG. 3 is a schematic front view showing a state where a holder to hold a flexible substrate is attached to an operation section main body equipped with a press unit in an operation section of the endoscope according to one embodiment.

As shown in FIG. 3, the operation section 12 includes the operation section main body (exterior case) 52 serving as an outer shell, an elastically deformable belt-shaped flexible substrate 54 which is disposed inside the operation section main body 52 and which has a switch function, and a holder (substrate frame) 56 which is disposed inside the operation section main body 52 and which fixes the flexible substrate 54. The operation section 12 further includes the press unit 58 which can independently press each of later-described first and second key portions 104 and 106. As shown in FIG. 1, the operation section 12 includes a grasp portion 60 coupled to the operation section main body 52. The grasp portion 60 is grasped by a user together with the operation section main body 52. The grasp portion 60 is coupled to the proximal end of the flexible tubular portion 26 of the insertion section 14 via an anti-breakage portion 60a.

Figure 4:
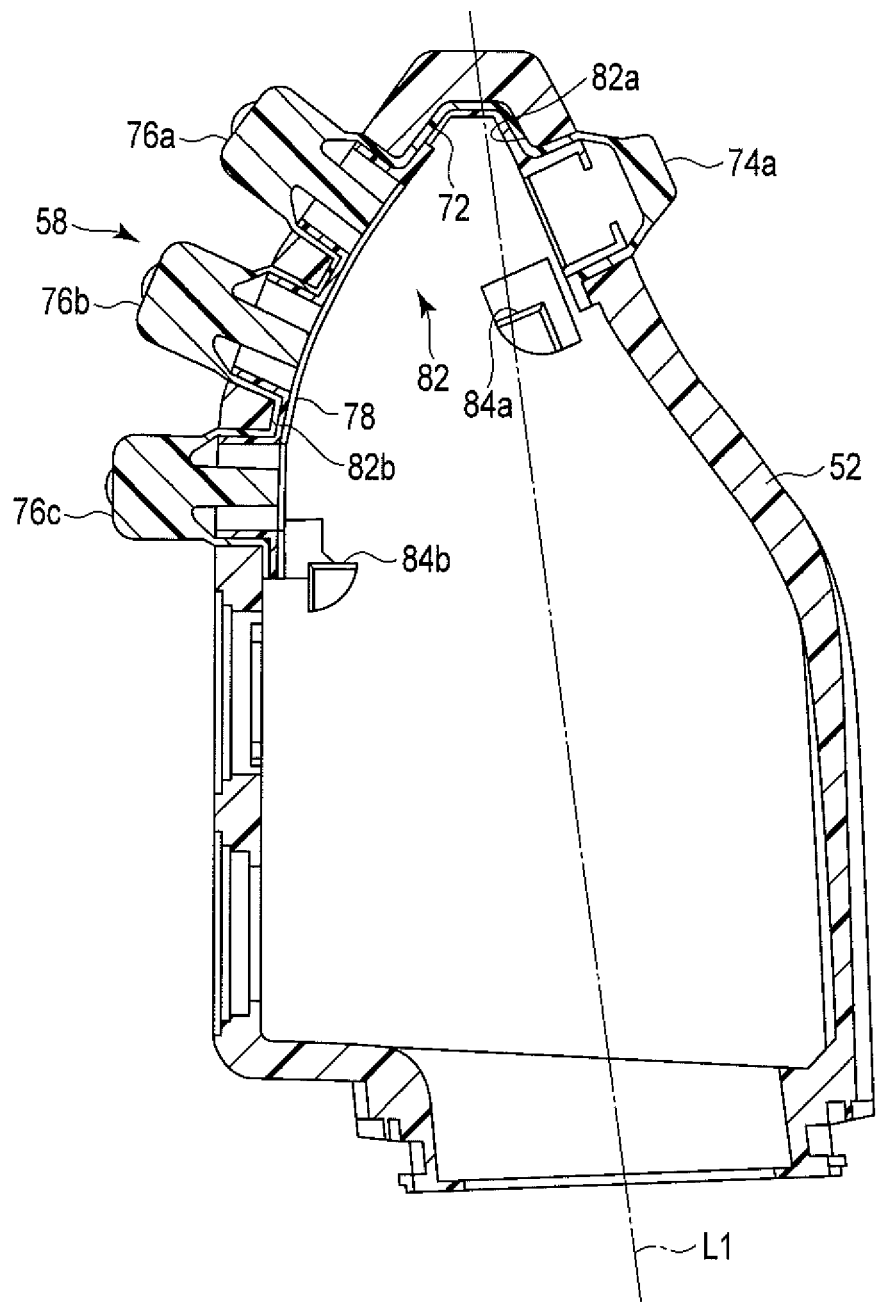
FIG. 4 is a schematic front view showing the operation section main body equipped with the press unit in the operation section of the endoscope according to one embodiment.

The operation section main body 52 shown in FIG. 3 and FIG. 4 cooperates with the grasp portion 60 to serve as the exterior case of the operation section 12. The operation section main body 52 is made of a heat-resistant, chemical-resistant, and insulating hard material such as denatured polyphenylether (PPE). The operation section main body 52 has a holder attachment portion 82, supporting columns 84a and 84b, and a lid portion 86 (see FIG. 1).

The holder attachment portion 82 is formed inside the operation section main body 52. The holder attachment portion 82 defines an internal space of the operation section main body 52. The holder 56 is provided in the holder attachment portion 82 in a state where the flexible substrate 54 is held to the upper end (proximal end) on the upper side (the proximal side along the longitudinal direction L1) of the operation section main body 52. That is, the holder 56 is provided inside the operation section main body 52 in a state where the flexible substrate 54 is held.

The holder attachment portion 82 includes first and second inner facing surfaces 82a and 82b. The first and second inner facing surfaces 82a and 82b face each other.

The press unit 58 is fitted and attached to the first and second inner facing surfaces 82a and 82b. The first and second inner facing surfaces 82a and 82b hold therebetween the holder 56 to which the flexible substrate 54 is held. The first and second inner facing surfaces 82a and 82b may be formed as flat surfaces or curved surfaces. The angle between the first and second inner facing surfaces 82a and 82b is preferably formed as, for example, an acute angle. When the press unit 58 is attached to the operation section main body 52 and when the holder 56 to which the flexible substrate 54 is held is attached, the first inner facing surface 82a faces a first outer facing surface 142 of a body 132 of the holder 56, and the second inner facing surface 82b faces a second outer facing surface 144 of the body 132 of the holder 56.

The operation section main body 52 has the supporting columns 84a and 84b which support the holder 56 at a position on the proximal side (the upper end in FIG. 3) of the insertion section 14 along the longitudinal direction L1 to keep a state where the holder 56 is provided in (supported on) the holder attachment portion 82.

Although not shown, a rotation knob to curve the curving portion 24 is provided outside the operation section main body 52, and a known bending drive mechanism which rotates together with the rotation of the rotation knob is provided inside the operation section main body 52. In a state where these mechanisms are provided, the operation section main body 52 is covered with the lid portion 86.

Switching vales 62 and 64 of a water/air supply unit and a suction unit are provided in the operation section main body 52. The switching vales 62 and 64 are provided in parallel in the later-described second press portion 76.

It is preferable that the press unit 58 includes an integral plate 72, and the first and second press portions 74 and 76. The plate 72 and the first and second press portions 74 and 76 are made of a heat-resistant and insulating soft resin material such as a silicone resin material. That is, the plate 72 and the first and second press portions 74 and 76 are materials that are flexible enough for the operation section main body 52.

Here, as shown in FIG. 4, the press unit 58 includes a holding member 78 which holds the plate 72 and the first and second press portions 74 and 76 to the operation section main body 52. The holding member 78 is formed into a substantially rectangular shape using a heat-resistant and insulating hard resin material such as polypropylene. The holding member 78 is made of a material that is harder than the press portions 74 and 76 and softer than the operation section main body 52.

The first press portion 74 has a press body 74a which is operated by the thumb of the left hand of the user when the operation section 12 is grasped with, for example, the left hand of the user of the endoscope 10. The second press portion 76 has first to third press bodies 76a, 76b, and 76c which are suitably operated by the first finger and second finger of the user's left hand when the operation section 12 is grasped with, for example, the left hand of the user of the second endoscope 10.

A later-described key body 104a of the flexible substrate 54 faces the press body 74a of the first press portion 74. Later-described key bodies 106a, 106b, and 106c of the flexible substrate 54 face the press bodies 76a, 76b, and 76c of the second press portion 76, respectively.

The press bodies 74a, 76a, 76b, and 76c are preferably configured to cooperate with the key bodies 104a, 106a, 106b, and 106c to provide a click feel to the user when the press bodies 74a, 76a, 76b, and 76c are pressed toward the key bodies 104a, 106a, 106b, and 106c.

Figure 5A:
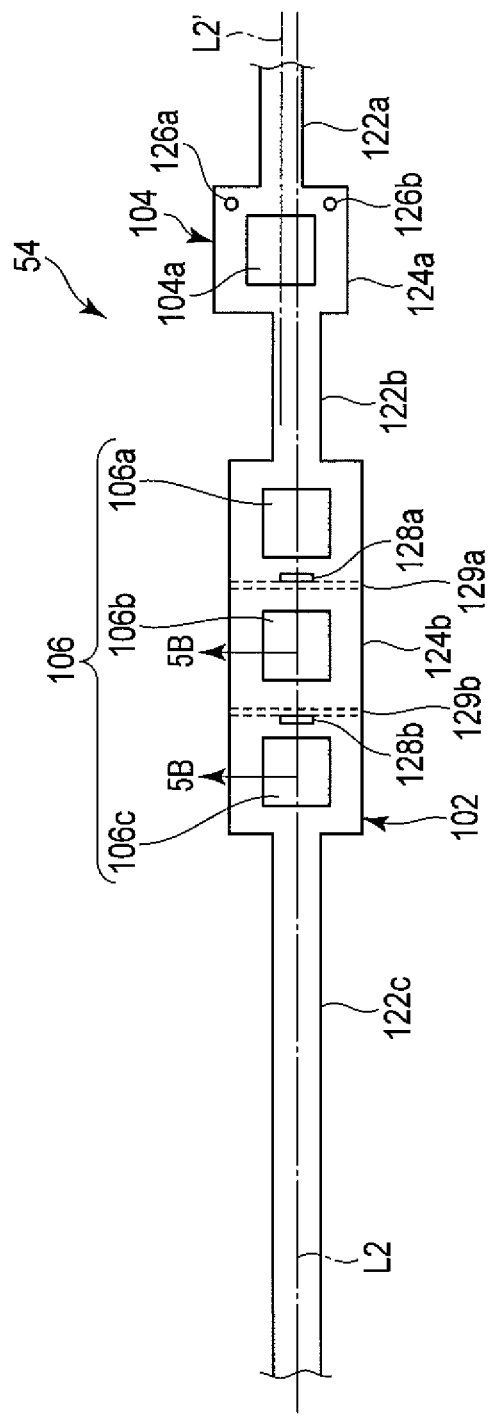
FIG. 5A is a schematic diagram showing the flexible substrate provided inside the operation section of the endoscope according to one embodiment.
Figure 5B:
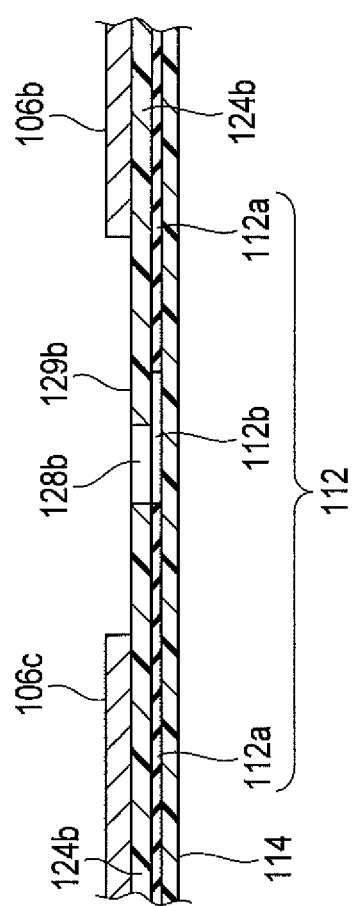
FIG. 5B is a schematic sectional view taken along the line 5B-5B in FIG. 5A.

The flexible substrate 54 shown in FIG. 5A and FIG. 5B are belt-shaped and elastically deformable. The flexible substrate 54 has a base material 102 in which unshown conducting wires are provided, the first and second key portions 104 and 106 which are disposed on the front surface of the base material 102 and which are pressed from the outside of the operation section main body 52 and thereby operated, a first adhesive portion (not shown) formed on the surface (the rear surface of the base material 102) of the base material 102 opposite to the first key portion 104, a first mold release sheet 110 (see FIG. 13A) attached to the first adhesive portion, a second adhesive portion 112 formed on the surface (the rear surface of the base material 102) opposite to the second key portion 106, and a second mold release sheet 114 attached to the second adhesive portion 112. Double-sided tape may be used as the first adhesive portion and the second adhesive portion 112.

The base material 102 of the flexible substrate 54 is preferably formed into a flexible belt shape using, for example, a polyimide resin material or a polyethylene resin material. The base material 102 is adhesively bonded to and wound around the holder 56.

The base material 102 of the flexible substrate 54 includes flexible first to third belt-shaped portions 122a, 122b, and 122c, a first key attachment portion 124a in which the first key portion 104 is provided, and a second key attachment portion 124b in which the second key portion 106 is provided. The first key attachment portion 124a is provided between the first and second belt-shaped portions 122a and 122b. The second key attachment portion 124b is provided between the second and third belt-shaped portions 122b and 122c. That is, the flexible second belt-shaped portion 122b is provided between the first and second key attachment portions 124a and 124b.

Here, the first belt-shaped portion 122a, the first key attachment portion 124a, the second belt-shaped portion 122b, the second key attachment portion 124b, and the third belt-shaped portion 122c are provided along a longitudinal direction L2 of the flexible substrate 54. Here, the first key attachment portion 124a is displaced relative to the second key attachment portion 124b in a direction that intersects at right angles with the longitudinal direction L2. More specifically, central axes L2' of the first belt-shaped portion 122a and the first key attachment portion 124a are provided coaxially with each other in the longitudinal direction L2. Central axes (the longitudinal direction L2) of the second belt-shaped portion 122b, the second key attachment portion 124b, and the third belt-shaped portion 122c are provided coaxially with each other in the longitudinal direction L2. The central axis L2' of the first key attachment portion 124a is provided to be displaced parallel to the central axis (the longitudinal direction L2) of the second key attachment portion 124b.

Each of the belt-shaped portions 122a, 122b, and 122c has a width smaller than the width (a width in the direction that intersects at right angles with the longitudinal direction L2) of each of the key attachment portions 124a and 124b. In contrast, each of the belt-shaped portions 122a, 122b, and 122c is sufficiently thinner than the width thereof. Therefore, each of the belt-shaped portions 122a, 122b, and 122c minimizes twisting and can yet be easily bent in two directions opposite to each other. Specifically, the second belt-shaped portion 122b can be bent and deformed so that the rear surfaces of the key attachment portions 124a and 124b substantially face each other.

The length of each of the belt-shaped portions 122a, 122b, and 122c along the longitudinal direction L2 is suitably adjusted. The length of the second belt-shaped portion 122b along the longitudinal direction L2 in particular is adjusted so that the second belt-shaped portion 122b is loosely provided between a ceiling portion 138a and a bottom surface portion 138b, described later, without contacting the ceiling portion 138a and the bottom surface portion 138b.

The first key portion 104 has the key body 104a which faces the press body 74a of the first press portion 74. The key body 104a is formed on one surface (front surface) of the first key attachment portion 124a.

The second key portion 106 has the first key body 106a which faces the first press body 76a of the second press portion 76, the second key body 106b which faces the second press body 76b of the second press portion 76, and the third key body 106c which faces the third press body 76b of the second press portion 76. The key bodies 106a, 106b, and 106c are formed on one surface (front surface) of the second key attachment portion 124b. That is, all the key bodies 104a, 106a, 106b, and 106c are provided on one surface (the same surface) of the base material 102.

The key bodies 104a, 106a, 106b, and 106c are electrically connected to the connector 34 of the universal cord 32. For example, if the key body 104a is pressed, a control signal is transmitted to an unshown control unit through the connector 34. Similarly, if each of the first to third key bodies 106a, 106b, and 106c is pressed, each of different control signals is transmitted to the unshown control unit through the connector 34. Thus, the illumination optical system 42 and/or the observation optical system 44 can suitably be operated by pressing the key bodies 104a, 106a, 106b, and 106c.

First engagement recesses (engagement portions) 126a and 126b which can engage with first engagement protrusions (engagement protrusions) 186a and 186b formed in a later-described first attachment surface 152 of the holder 56 are formed in the first key attachment portion 124a. The first engagement recesses (engagement recesses) 126a and 126b are formed as, for example, circular openings. The first key attachment portion 124a is attached in a state to be positioned in the first attachment surface 152. Here, the two first engagement recesses 126a and 126b are separate from each other in the direction that intersects at right angles with the longitudinal direction L2 of the flexible substrate 54.

Second engagement recesses (engagement portions) 128a and 128b which can engage with second engagement protrusions (second engagement portions) 188a and 188b formed in a later-described second attachment surface 154 of the holder 56 are formed in the second key attachment portion 124b. The second engagement recesses 128a and 128b are formed as, for example, oblong openings. The second key attachment portion 124b is attached in a state to be positioned in the second attachment surface 154. Here, the two second engagement recesses 128a and 128b are separate from each other along the longitudinal direction L2 of the flexible substrate 54.

As shown in FIG. 5A, the second key attachment portion 124b has a first abutment position 129a at a position to abut on a later-described first bent portion 156a of the second attachment surface 154, and has a second abutment position 129b at a position to abut on a second bent portion 156b.

As shown in FIG. 5B, the second adhesive portion 112 has a coated portion 112a which is coated with an adhesive agent, and an uncoated portion 112b which is not coated with the adhesive agent. The coated portion 112a is formed around the second engagement recesses 128a and 128b and the first and second abutment positions 129a and 129b. In contrast, the uncoated portion 112b having no adhesive agent in the second adhesive portion 112 is formed at positions corresponding to the insides of the second engagement recesses 128a and 128b and positions corresponding to the first and second abutment positions 129a and 129b. That is, the first and second abutment positions 129a and 129b are not coated with the adhesive agent. The second mold release sheet 114 covers the whole second adhesive portion 112 including the coated portion 112a and the uncoated portion 112b with one sheet-shaped material. That is, the flexible substrate 54 has, in the surface of the second key attachment portion 124b opposite to the surface to which the second key portion 106 is attached, the coated portion 112a which is coated with an attachment agent such as an adhesive agent to the second attachment surface 154, the uncoated portion 112b which is not coated in parts corresponding to the abutment positions 129a and 129b, and the mold release sheet 114 which integrally covers the coated portion 112a and the uncoated portion 112b and can be released from the coated portion 112a.

Thus, as compared to the case where the second mold release sheet is separated into parts, work can be easily done when the second key attachment portion 124b of the flexible substrate 54 according to this embodiment is attached to the second attachment surface 154.

The holder 56 shown in FIG. 6A to FIG. 9 is made of a heat-resistant and insulating hard resin material such as polypropylene. The holder 56 is made of a material which is harder than the plate 72 and the holding member 78 of the press unit 58 and which has about the same hardness as the operation section main body 52. That is, the operation section main body 52 and the holder 56 may have the same hardness, the operation section main body 52 may be harder than the holder 56, or the operation section main body 52 may be softer than the holder 56.

As shown in FIG. 6A to FIG. 7B, the holder 56 includes the body 132, first and second openings (opening edges) 134 and 136, and a cavity portion 138 to dispose the flexible substrate 54 in a bent state inside the holder 56.

The body 132 has leg portions 132a and 132b which are supported on the supporting columns 84a and 84b provided in the holder attachment portion 82 of the operation section main body 52. As indicated by a sign 132c, the part between the leg portions 132a and 132b is continuously formed by a smooth flat surface of a curved surface.

The body 132 is preferably block-shaped to exert a press force to press the inner circumferential surface of the operation section main body (exterior case) 52 to the outside, but may be substantially V-shaped depending on the selection of materials. In this embodiment, the body 132 of the holder 56 is block-shaped, and has holes 132d that reduce its weight while maintaining strength.

The body 132 has the first and second outer facing surfaces 142 and 144 facing the press unit 58, and first and second side surfaces 146 and 148 which are provided between the first and second outer facing surfaces 142 and 144 (the later-described first and second attachment surfaces 152 and 154) and which separate from each other. The angle between the first and second outer facing surfaces 142 and 144 is preferably an acute angle. The first and second side surfaces 146 and 148 are preferably, for example, parallel to each other. Each of the first and second outer facing surfaces 142 and 144 and each of the first and second side surfaces 146 and 148 are adjacent to a top (coupling surface) 150. That is, the top 150 is provided between the first and second outer facing surfaces 142 and 144. The top 150 is also provided between the first and second side surfaces 146 and 148. That is, the top 150 is provided between the first and second outer facing surfaces 142 and 144 (the first and second attachment surfaces 152 and 154) and between the first and second side surfaces 146 and 148.

The first attachment surface 152 to which the first key attachment portion 124a of the flexible substrate 54 is attached is formed in the first outer facing surface 142. The first attachment surface 152 is recessed relative to the first outer facing surface 142. The width of the first attachment surface 152 that intersects at right angles with a longitudinal direction L3 is preferably formed to be slightly larger than the width of the first key attachment portion 124a of the flexible substrate 54.

The second attachment surface 154 to which the second key attachment portion 124b of the flexible substrate 54 is attached is formed in the second outer facing surface 144. The second attachment surface 154 is recessed relative to the second outer facing surface 144. The width of the second attachment surface 154 that intersects at right angles with the longitudinal direction L3 is preferably formed to be slightly larger than the width of the second key attachment portion 124b of the flexible substrate 54.

In this embodiment, the first key attachment portion 124a of the flexible substrate 54 is displaced in the direction that intersects at right angles with the longitudinal direction L2 thereof. Thus, the edge of the first attachment surface 152 is closer to the first side surface 146 than the edge of the second attachment surface 154. In other words, the distance between the first attachment surface 152 and the first side surface 146 is smaller than the distance between the second attachment surface 154 and the first side surface 146.

The second attachment surface 154 includes a first attachment region 154a which fixes the rear surface of the part of the second key attachment portion 124b in which the first key body 106a is provided, a second attachment region 154b which fixes the rear surface of the part in which the second key body 106b is provided, and a third attachment region 154c which fixes the rear surface of the part in which the third key body 106c is provided. The attachment regions 154a, 154b, and 154c are provided along the longitudinal direction L3 in this order. Each of the first to third attachment regions 154a, 154b, and 154c is preferably formed into a flat surface. Thus, the press unit 58 can independently press the second key portion 106.

The second attachment surface 154 preferably has the bent portions 156a and 156b. The first bent portion 156a is formed between the first and second attachment regions 154a and 154b. The second bent portion 156b is formed between the second and third attachment regions 154b and 154c. The first bent portion 156a brings the normal to the second attachment region 154b closer to a state to intersect at right angles with the longitudinal direction L1 than the first attachment region 154a. The second bent portion 156b brings the normal to the third attachment region 154c closer to a state to intersect at right angles with the longitudinal direction L1 than the second attachment region 154b.

Figure 8A:
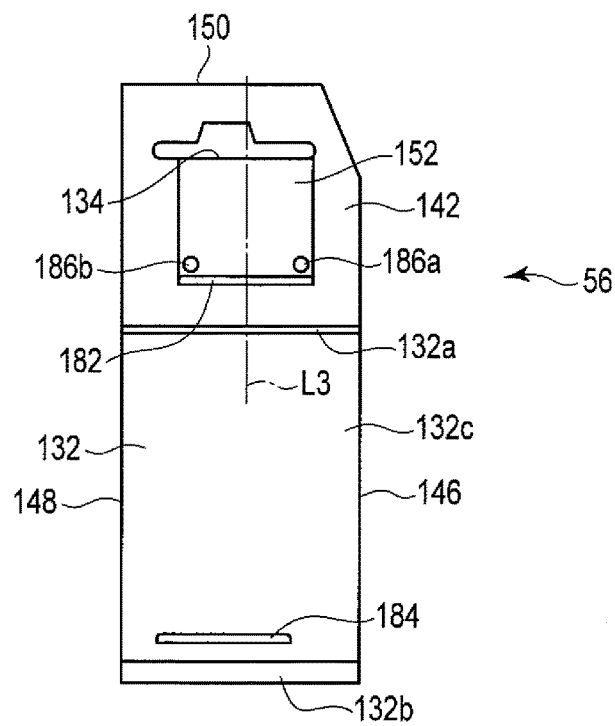
FIG. 8A is a schematic plan view showing a first attachment surface of the holder provided inside the operation section of the endoscope according to one embodiment.
Figure 8B:
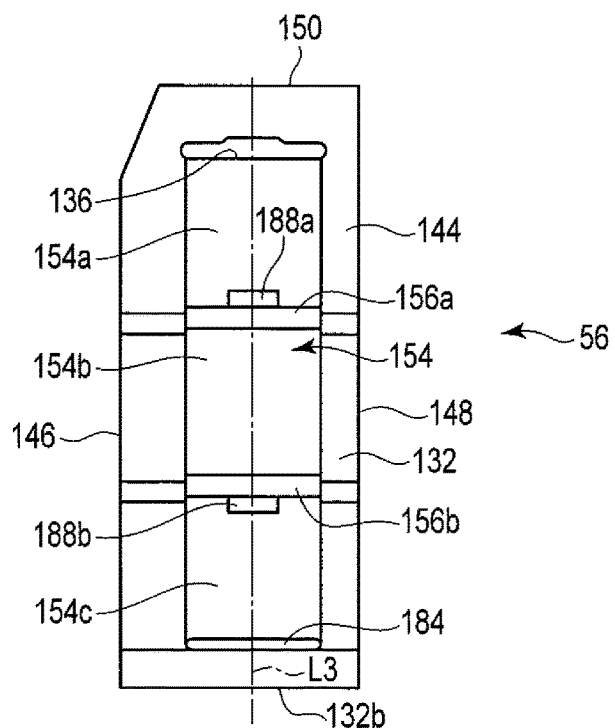
FIG. 8B is a schematic plan view showing a second attachment surface of the holder provided inside the operation section of the endoscope according to one embodiment.

As shown in FIG. 8A and FIG. 8B, the first and second attachment surfaces 152 and 154 are formed substantially in the center of the width direction that intersects at right angles with the longitudinal direction L3 in the first and second outer facing surfaces 142 and 144, respectively. Specifically, the edges of the first and second attachment surfaces 152 and 154 are formed to be displaced in the width direction in accordance with the displacement of the first and second key attachment portions 124a and 124b relative to the longitudinal direction L2 of the flexible substrate 54 shown in FIG. 5.

In the body 132, the first opening 134 is formed at the upper end of the first attachment surface 152, that is, at the end close to the top 150, and the second opening 136 is formed at the upper end of the second attachment surface 154, that is, at the end close to the top 150.

A first passage 182 which brings the first belt-shaped portion 122a of the flexible substrate 54 toward the lower side of the body 132 of the holder 56 is formed at the lower end (the end separate from the top 150) of the first attachment surface 152. A second passage 184 which brings the third belt-shaped portion 122c of the flexible substrate 54 toward the lower side of the body 132 of the holder 56 is formed at the lower end (the end separate from the top 150) of the second attachment surface 154.

The first engagement protrusions 186a and 186b are formed in the first attachment surface 152. Each of the first engagement protrusions 186a and 186b is, for example, disk-shaped or column-shaped. The first engagement protrusions 186a and 186b are separate in the width direction that intersects at right angles with the longitudinal direction L3 of the first attachment surface 152. The first engagement recesses 126a and 126b of the first key attachment portion 124a of the flexible substrate 54 can be positioned on the first engagement protrusions 186a and 186b of the first attachment surface 152.

The second engagement protrusions 188a and 188b are formed in the second attachment surface 154. Each of the second engagement protrusions 188a and 188b is formed, for example, into a columnar shape having an elliptic edge. The second engagement protrusions 188a and 188b are separate along the longitudinal direction L3 of the second attachment surface 154. The second engagement recesses 128a and 128b of the second key attachment portion 124b of the flexible substrate 54 can be positioned on the second engagement protrusions 188a and 188b of the second attachment surface 154.

Figure 9:
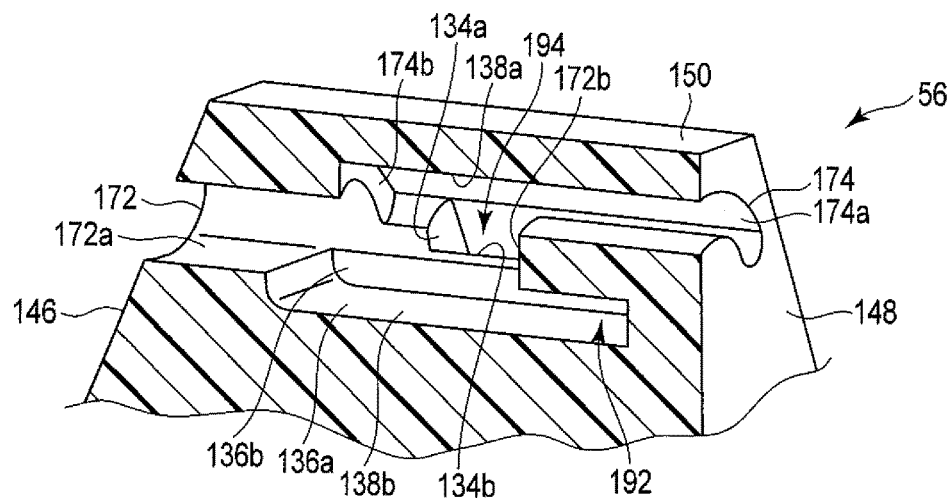
FIG. 9 is a schematic sectional view of the vicinity of the top of the holder provided inside the operation section of the endoscope according to one embodiment, taken along the line IX-IX in FIG. 7A.

As shown in FIG. 9, the cavity portion 138 communicates with the first and second openings 134 and 136. The cavity portion 138 has, in its inner circumferential surface (the inner circumferential surface of the holder 56), the ceiling portion 138a formed closer to the upper side (proximal side) along the longitudinal direction L1 than the first and second openings 134 and 136, that is, at a position closer to the top 150. The cavity portion 138 also has the bottom surface portion 138b facing the ceiling portion 138a. The bottom surface portion 138b is formed as the bottom surface of the second opening 136. That is, the cavity portion 138 has the bottom surface portion 138b which is closer to the lower edge than the ceiling portion 138a, that is, located on the side separate from the top 150 and which faces the ceiling portion 138a and which houses the second belt-shaped portion 122b in a separate state.

Here, a first recess 134a which is continuous with the first opening 134 and which has the same shape as the first opening 134 is formed in a direction that intersects, for example, at right angles or substantially at right angles with the longitudinal direction L1 of the insertion section 14 of the endoscope 10. An opening edge having the same shape as the first opening 134 is not formed in the second attachment surface 154. That is, the first opening 134 has the same shape in the direction that intersects at right angles or substantially at right angles with the longitudinal direction L1, and does not pierce from the first attachment surface 152 to the second attachment surface 154. In this way, it is preferable that the shape is the same from the first opening 134 to a distal end 134b of the first recess 134a to the first opening 134. For example, between the first attachment surface 152 and the second attachment surface 154, a space which is continuous with the first opening 134 is formed in a region located substantially ⅓ of the distance from the first attachment surface 152 to the second attachment surface 154. Such a space is preferably formed by a die, but may be formed by a removal process.

A second recess 136a which is continuous with the second opening 136 and which has the same shape as the second opening 136 is formed in a direction that intersects, for example, at right angles or substantially at right angles with the longitudinal direction L1. An opening edge having the same shape as the second opening 136 is not formed in the first attachment surface 152. That is, the second opening 136 has the same shape in the direction that intersects at right angles or substantially at right angles with the longitudinal direction L1, and does not pierce from the second attachment surface 154 to the first attachment surface 152. In this way, it is preferable that the shape is the same from the second opening 136 to a distal end 136b of the second recess 136a to the second opening 136. For example, between the second attachment surface 154 and the first attachment surface 152, a space which is continuous with the second opening 136 is formed in a region located substantially ⅔ from the second attachment surface 154 to the first attachment surface 152. Such a space is preferably formed by a die, but may be formed by a removal process.

In the body 132, a third opening (opening edge) 172 (see FIG. 6A and FIG. 6B) which communicates with the cavity portion 138 at the upper edge of the first side surface 146 is formed, and a fourth opening (opening edge) 174 (see FIG. 7A and FIG. 7B) which communicates with the cavity portion 138 at the upper edge of the second side surface 148 is formed. That is, the third opening 172 which communicates with the cavity portion 138 is formed in the first side surface 146, and the fourth opening 174 which communicates with the cavity portion 138 and which is continuous with the ceiling portion 138a is formed in the second side surface 148.

A third recess 172a which is continuous with the third opening 172 and which has the same shape as the third opening 172 is formed in a direction that intersects, for example, at right angles or substantially at right angles with the longitudinal direction L1. An opening edge having the same shape as the third opening 172 is not formed in the second side surface 148. That is, the third opening 172 has the same shape in the direction that intersects at right angles or substantially at right angles with the longitudinal direction L1, and does not pierce from the first side surface 146 to the second side surface 148. In this way, it is preferable that the shape is the same from the third opening 172 to a distal end 172b of the third recess 172a to the third opening 172. For example, between the first side surface 146 and the second side surface 148, a space which is continuous with the third opening 172 is formed in a region located substantially ⅔ of the distance from the first side surface 146 to the second side surface 148. Such a space is preferably formed by a die, but may be formed by a removal process.

A fourth recess 174a which is continuous with the fourth opening 174 and which has the same shape as the fourth opening 174 is formed in a direction that intersects, for example, at right angles or substantially at right angles with the longitudinal direction L1. An opening edge having the same shape as the fourth opening 174 is not formed in the first side surface 146. That is, the fourth opening 174 has the same shape in the direction that intersects at right angles or substantially at right angles with the longitudinal direction L1, and does not pierce from the second side surface 148 to the first side surface 146. In this way, it is preferable that the shape is the same from the fourth opening 174 to a distal end 174b of the fourth recess 174a to the fourth opening 174. For example, between the first side surface 146 and the second side surface 148, a space which is continuous with the fourth opening 174 is formed in a region located substantially ⅔ the distance from the second side surface 148 to the first side surface 146. Such a space is preferably formed by a die, but may be formed by a removal process.

As shown in FIG. 6B, FIG. 7B, FIG. 8A, and FIG. 9, the first opening 134 and the first recess 134a have a width (opening amount) greater than the width of the first attachment surface 152 of the flexible substrate 54 that intersects at right angles with the longitudinal direction L3, and are substantially T-shaped to dispose the second belt-shaped portion 122b of the flexible substrate 54. As shown in FIG. 8B and FIG. 9, the second opening 136 and the second recess 136a have a width (opening amount) greater than the width of the second attachment surface 154 of the flexible substrate 54 that intersects at right angles with the longitudinal direction L3.

As shown in FIG. 6A, FIG. 6B, and FIG. 9, the third opening 172 and the third recess 172a are formed into a substantially triangular shape. As shown in FIG. 7A, FIG. 7B, and FIG. 9, the fourth opening 174 and the fourth recess 174a are substantially U-shaped or substantially V-shaped.

The first to fourth recesses 134a, 136a, 172a, and 174a cooperate to form the cavity portion 138.

The fourth opening 174 is continuous with the ceiling portion 138a. The second opening 136 is continuous with the bottom surface portion 138b. The cavity portion 138 is formed by the third recess 172a to secure the space of a cavity for the second belt-shaped portion 122b of the flexible substrate 54, and is formed by the fourth recess 174a to increase the distance of the ceiling portion 138a from the bottom surface portion 138b.

As shown in FIG. 9, the distal end 172b to the third opening 172 and the distal end 174b to the fourth opening 174 are formed by the third and fourth recesses 172a and 174a. The space between the distal ends 172b and 174b, that is, the width of the ceiling portion 138a has a width greater than the width of the second belt-shaped portion 122b of the flexible substrate 54 that intersects at right angles with the longitudinal direction L2.

The cavity portion 138 according to this embodiment has a guide portion 192 which guides the flexible substrate 54, and a housing portion (housing space) 194 which houses the second belt-shaped portion 122b of the flexible substrate 54. The guide portion 192 and the housing portion 194 are adjacent to each other.

The guide portion 192 guides the first belt-shaped portion 122a and the first key attachment portion 124a of the flexible substrate 54 into the cavity portion 138 from the outside of the body 132 through the second opening 136, and guides the first belt-shaped portion 122a and the first key attachment portion 124a of the flexible substrate 54 to the outside of the body 132 from the inside of the cavity portion 138 through the first opening 134. The first opening 134 and the second opening 136 allow the flexible substrate 54 to be passed into the holder 56 from the outside of the holder 56, and allow the flexible substrate 54 to be passed to the outside of the holder 56 from the inside of the holder 56.

The housing portion 194 has the bottom surface portion 138b which is closer to the lower end (the position separate from the top 150) along the longitudinal direction L1 than the ceiling portion 138a and which faces the ceiling portion 138a. The bottom surface portion 138b is continuous with the third recess 172a of the third opening 172. The ceiling portion 138a is continuous with the fourth recess 174a of the fourth opening 174. The housing portion 194 cooperates with the guide portion 192 to guide the flexible substrate 54 and form a space in which the second belt-shaped portion 122b is bent between the bottom surface portion 138b and the ceiling portion 138a and in which the second belt-shaped portion 122b can be housed separately from the ceiling portion 138a when the first key attachment portion 124a is attached to the first attachment surface 152 from the second opening 136 to the first opening 134 through the flexible substrate 54 and when the second key attachment portion 124b is attached to the second attachment surface 154. It is preferable that the second belt-shaped portion 122b being housed in the housing portion 194 is not only separate from the ceiling portion 138a but also separate from the bottom surface portion 138b. That is, the second belt-shaped portion 122b is not being supported on the holder 56 (is floating).

In this embodiment, it is preferable that the guide portion 192 is located closer to the second side surface 148 than the first side surface 146 and the housing portion 194 is located closer to the first side surface 146 than the second side surface 148 because the first and second key attachment portions 124a and 124b of the flexible substrate 54 are displaced in the direction that intersects at right angles with the longitudinal direction L2 of the flexible substrate 54.

Next, a manufacturing process to attach the flexible substrate 54 to the holder 56 according to this embodiment and attach the holder 56 to which the flexible substrate 54 is attached to the operation section main body 52 in which the press unit 58 is provided is briefly described.

Figure 10:
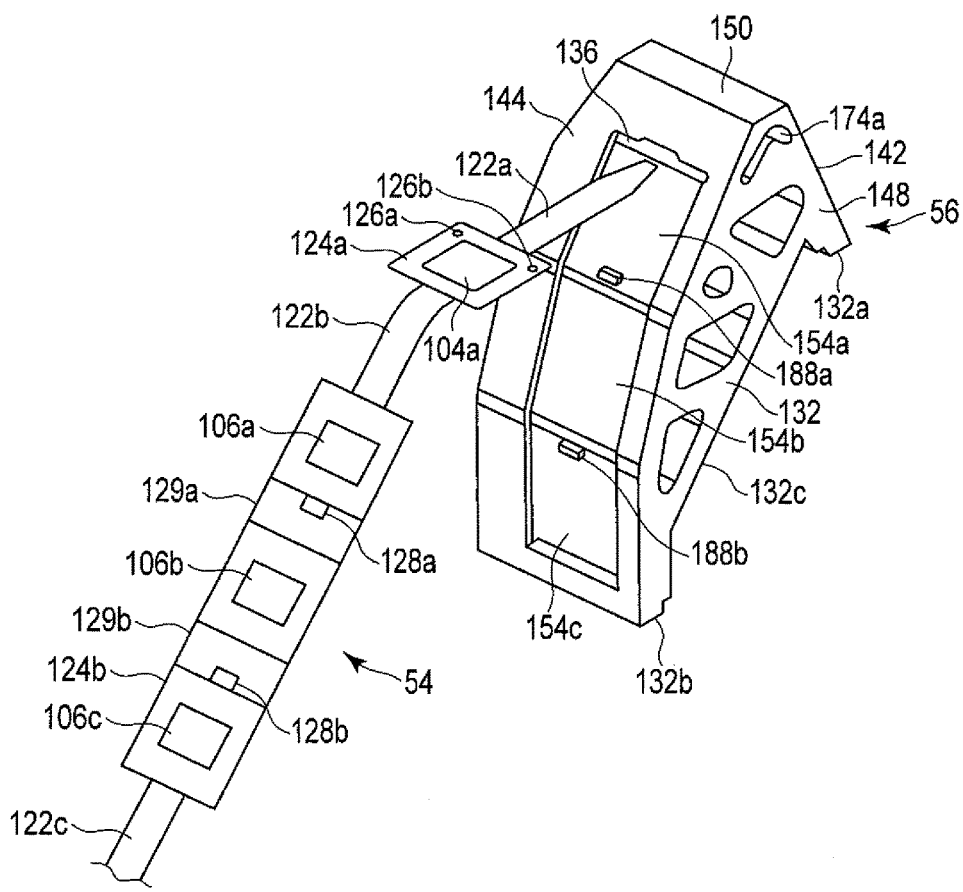
FIG. 10 is a schematic perspective view showing a state where a first belt-shaped portion of the flexible substrate is placed to face a second opening of the holder provided inside the operation section of the endoscope according to one embodiment.

As shown in FIG. 10, the end of the first belt-shaped portion 122a of the flexible substrate 54 is placed to face the second opening 136 of the second attachment surface 154 of the holder 56. Further, the end of the first belt-shaped portion 122a of the flexible substrate 54 is placed into the second opening 136 of the second attachment surface 154 of the holder 56, and the first belt-shaped portion 122a and the first key attachment portion 124a are then pulled out of the first opening 134 through the cavity portion 138.

Figure 11:
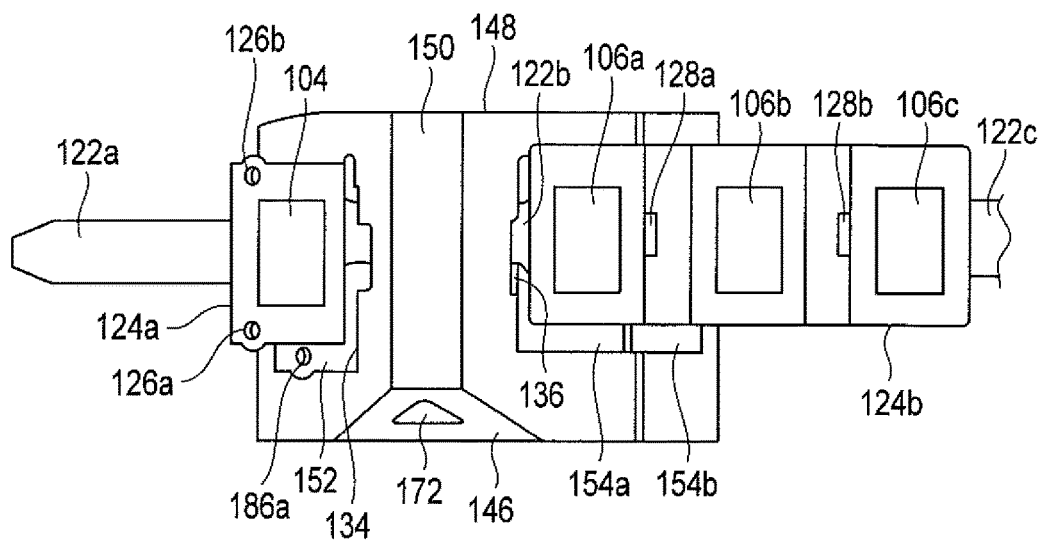
FIG. 11 is a schematic top view showing a state where the first belt-shaped portion and a first key attachment portion of the flexible substrate are protruded toward the first attachment surface through a first opening from a second opening of the holder provided inside the operation section of the endoscope according to one embodiment, and a second belt-shaped portion is disposed between the second opening and the first opening.
Figure 12:
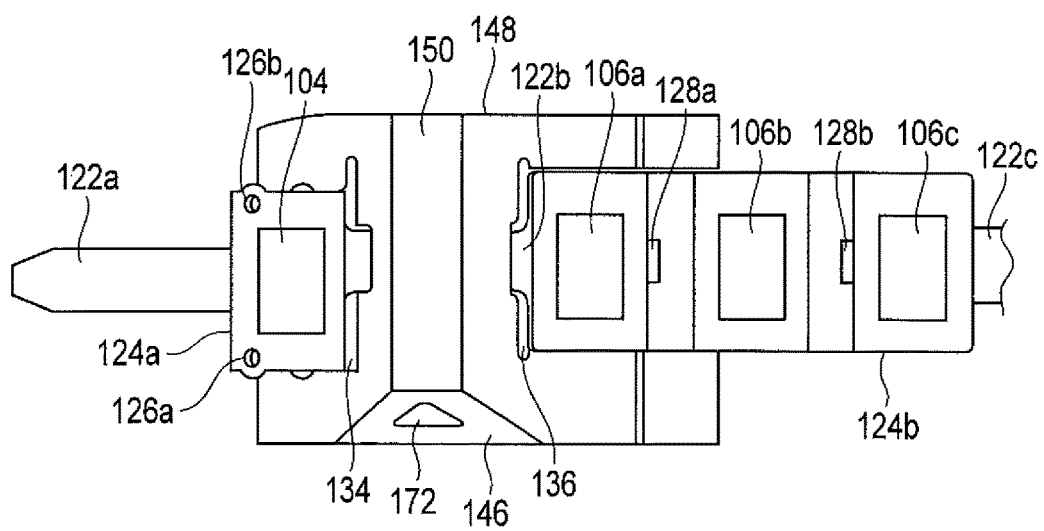
FIG. 12 is a schematic top view showing a state where the flexible substrate is moved in a direction that intersects at right angles with the longitudinal direction of the flexible substrate relative to the holder provided inside the operation section of the endoscope according to one embodiment, as compared to the state shown in FIG. 11.

In this instance, as shown in FIG. 11, the first key attachment portion 124a is displaced from the first attachment surface 152, and the second key attachment portion 124b is displaced from the second attachment surface 154. Thus, as shown in FIG. 12, in a state where the second belt-shaped portion 122b is provided in the cavity portion 138 between the first and second openings 134 and 136, the flexible substrate 54 is moved in the direction that intersects at right angles with the longitudinal direction L2 thereof and in the direction that intersects at right angles with the longitudinal direction L3 of the first and second attachment surfaces 152 and 154.

Figure 13A:
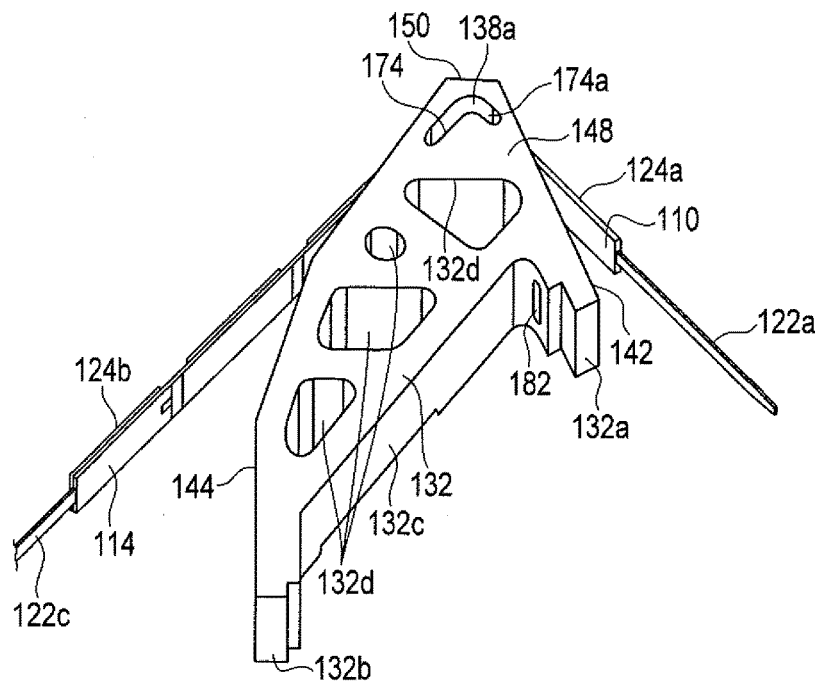
FIG. 13A is a schematic perspective view showing a state where the second belt-shaped portion of the flexible substrate is disposed between the first and second openings of the holder provided inside the operation section of the endoscope according to one embodiment.
Figure 13B:
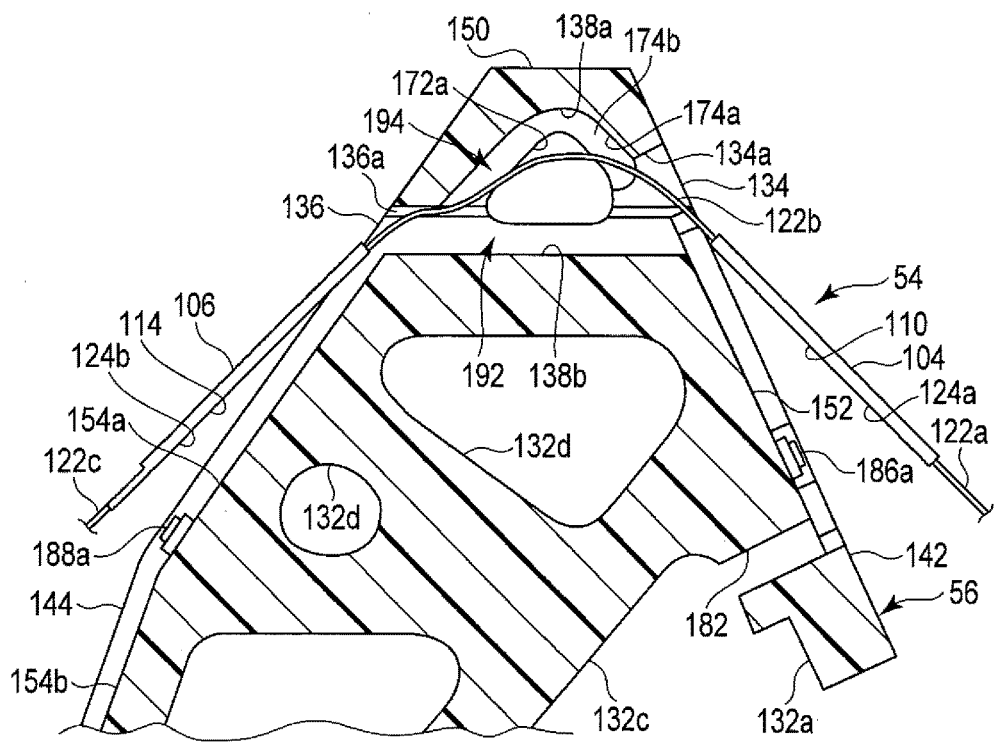
FIG. 13B is a schematic sectional view showing a state where the second belt-shaped portion of the flexible substrate is disposed between the first and second openings of the holder provided inside the operation section of the endoscope according to one embodiment.

In this instance, as shown in FIG. 13A and FIG. 13B, the second belt-shaped portion 122b is separate from the ceiling portion 138a of the cavity portion 138. The second belt-shaped portion 122b is separate from the bottom surface portion 138b of the cavity portion 138. Tensile force applied to the second belt-shaped portion 122b is minimized, and the second belt-shaped portion 122b is loose. The second belt-shaped portion 122b is disposed between the distal end 172b to the third opening 172 and the distal end 174b to the fourth opening 174.

In this state, the first mold release sheet 110 on the rear surface of the first key attachment portion 124a of the flexible substrate 54 is detached. Further, the first belt-shaped portion 122a of the flexible substrate 54 is placed into the first passage (lower end opening) 182 of the first attachment surface 152 and then guided to the rear surface of the first attachment surface 152, and the first engagement recesses 126a and 126b of the first key attachment portion 124a are engaged with the first engagement protrusions 186a and 186b of the first attachment surface 152. Thus, the rear surface of the first key attachment portion 124a is attached to the first attachment surface 152 by the first adhesive portion. Therefore, the key body 104a in the front surface of the first key attachment portion 124a is held to the first attachment surface 152.

Similarly, the second mold release sheet 114 (see FIG. 5B) on the rear surface of the second key attachment portion 124b of the flexible substrate 54 is detached. Further, the third belt-shaped portion 122c of the flexible substrate 54 is placed into the second passage (lower end opening) 184 of the second attachment surface 154 and then guided to the rear surface of the second attachment surface 154, and the second engagement recesses 128a and 128b of the second key attachment portion 124b are engaged with the second engagement protrusions 188a and 188b of the second attachment surface 154. Thus, the rear surface of the second key attachment portion 124b is attached to the second attachment surface 154 by the second adhesive portion 112. Therefore, the key bodies 106a, 106b, and 106c in the front surface of the second key attachment portion 124b are held to the second attachment surface 154. More specifically, the first key body 106a is held to the first attachment region 154a of the second attachment surface 154, the second key body 106b is held to the second attachment region 154b, and the third key body 106c is held to the third attachment region 154c.

In the case according to the present embodiment, the three key bodies 106a, 106b, and 106c are provided in the front surface of the second key attachment portion 124b, but one second mold release sheet 114 is provided on the rear surface of the second key attachment portion 124b. Thus, work can be more easily done to attach the second key attachment portion 124b to the second attachment surface 154 than when a mold release sheet is present on the rear side of each of the key bodies 106a, 106b, and 106c.

Figure 14A:
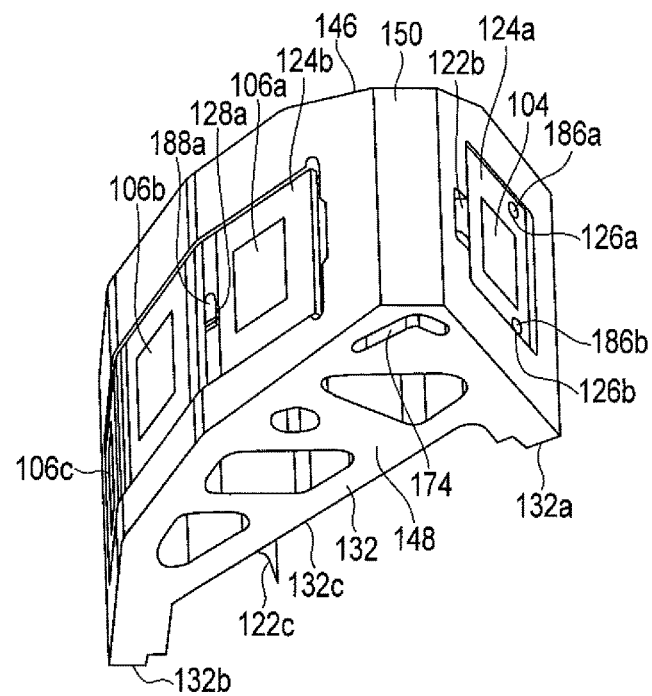
FIG. 14A is a schematic perspective view showing a state where while the second belt-shaped portion of the flexible substrate is disposed between the first and second openings of the holder provided inside the operation section of the endoscope according to one embodiment, the first belt-shaped portion is guided to a first passage, the first key attachment portion is attached to the first attachment surface, a third belt-shaped portion is guided to a second passage, and a second key attachment portion is attached to the second attachment surface.
Figure 14B:
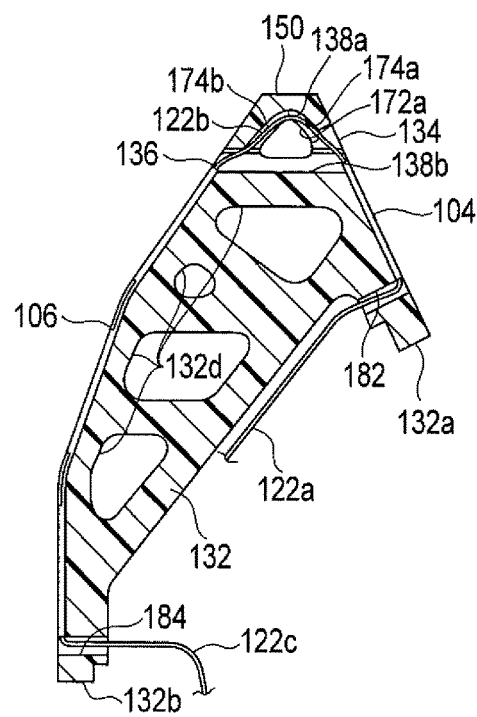
FIG. 14B is a schematic sectional view showing a state where while the second belt-shaped portion of the flexible substrate is disposed between the first and second openings of the holder provided inside the operation section of the endoscope according to one embodiment, the first belt-shaped portion is guided to the first passage, the first key attachment portion is attached to the first attachment surface, the third belt-shaped portion is guided to the second passage, and the second key attachment portion is attached to the second attachment surface.

As shown in FIG. 14A and FIG. 14B, the flexible substrate 54 is held by the holder 56 as above. At this point, as shown in FIG. 14B, the second belt-shaped portion 122b is separate from each of the ceiling portion 138a and the bottom surface portion 138b of the cavity portion 138. That is, in a state where the flexible substrate 54 protruding to the outside of the holder 56 from the first opening 134 and the second opening 136 is fixed to the outer circumference of the holder 56, the second belt-shaped portion 122b of the flexible substrate 54 is disposed separately from the ceiling portion 138a of the cavity portion 138 formed in the inner circumferential surface of the cavity portion 138. This prevents force that detaches the first and second key attachment portions 124a and 124b from the first and second attachment surfaces 152 and 154 from being continuously applied, for example, as in a state where the second belt-shaped portion is in abutment with the ceiling portion. Moreover, the second belt-shaped portion 122b is loose. This minimizes the application of tensile force to the second belt-shaped portion 122b.

The holder 56 holding the flexible substrate 54 is then provided in the holder attachment portion 82 of the operation section main body 52. In this instance, it is preferable to press the holder 56 into the operation section main body 52 in which the press unit 58 is provided to suppress the shaking of the holder 56 relative to the operation section main body 52 to the minimum. The leg portions 132a and 132b of the body 132 of the holder 56 are then engaged with the supporting columns 84a and 84b of the operation section main body 52. In this way, the holder 56 which holds the flexible substrate 54 is provided in the operation section main body 52.

At this point, the key body 104a faces the press body 74a, the key body 106a faces the first press body 76a, the key body 106b faces the second press body 76b, and the third key body 106c faces the third press body 76c. The third belt-shaped portion 122c is electrically connected to the connector 34 via a conducting wire provided in the universal cord 32.

A bending operation knob and a bending drive mechanism are then provided in a space at the lower end of the operation section main body 52.

In addition, after the grasp portion 60 and the universal cord 32 are attached to the operation section main body 52, the lid portion 86 is disposed in the operation section main body 52 to form the operation section 12. The insertion section 14 is suitably attached to the operation section 12 to form the endoscope 10.

The following can be said according to the endoscope 10 in this embodiment.

The cavity portion 138 of the holder 56 can guide the flexible substrate 54 into the cavity portion 138 from the outside of the body 132 through the second opening 136 and guide the flexible substrate 54 to the outside of the body 132 from the inside of the cavity portion 138 through the first opening 134. When the first key attachment portion 124a is attached to the first attachment surface 152 and the second key attachment portion 124b is attached to the second attachment surface 154, the second belt-shaped portion 122b can be housed separately from the ceiling portion 138a of the cavity portion 138. This can prevent the application of force to the second belt-shaped portion 122b, and minimize the application of force that detaches the first and second key attachment portions 124a and 124b from the first and second attachment surfaces 152 and 154 to the first and second key attachment portions 124a and 124b adjacent to the second belt-shaped portion 122b.

The second belt-shaped portion 122b of the flexible substrate 54 is floating with a proper degree of looseness to form spaces between the second belt-shaped portion 122b and both the ceiling portion 138a and the bottom surface portion 138b of the cavity portion 138. This not only minimizes the pressing of the second belt-shaped portion 122b by the ceiling portion 138a but can also prevent the force that detaches the first and second key attachment portions 124a and 124b from the first and second attachment surfaces 152 and 154 from being applied due to the application of tensile force to the first and second key attachment portions 124a and 124b because the length of the second belt-shaped portion 122b is too short.

Furthermore, it can be easily imagined that attachment work is difficult if the second belt-shaped portion 122b is pressed with the ceiling portion 138a when the first key attachment portion 124a of the flexible substrate 54 is attached to the first attachment surface 152 of the holder 56 and when the second key attachment portion 124b of the flexible substrate 54 is attached to the second attachment surface 154 of the holder 56. In contrast, in this embodiment, the ceiling portion 138a and the second belt-shaped portion 122b are separate from each other even when the first key attachment portion 124a of the flexible substrate 54 is attached to the first attachment surface 152 of the holder 56 and when the second key attachment portion 124b of the flexible substrate 54 is attached to the second attachment surface 154 of the holder 56. Thus, workability of positioning and attachment can be improved when the first key attachment portion 124a of the flexible substrate 54 is attached to the first attachment surface 152 of the holder 56 and when the second key attachment portion 124b of the flexible substrate 54 is attached to the second attachment surface 154 of the holder 56.

Therefore, according to this embodiment, it is possible to provide the endoscopic operation section 12 and the endoscope 10 which can keep the key portions 104 and 106 of the flexible substrate 54 disposed at desired positions of the holder 56.

Here, the three key bodies 106a, 106b, and 106c can be positioned merely by detaching one second mold release sheet 114 of the second key attachment portion 124b of the flexible substrate 54 having the key bodies 106a, 106b, and 106c and then attaching the key bodies 106a, 106b, and 106c to predetermined attachment positions of the second attachment surface 154. Thus, the time for the manufacturing operation can be reduced as compared to the case where the rear surface of the second key attachment portion 124b in which each of the key bodies 106a, 106b, and 106c is provided is positioned at each of the first to third attachment regions 154a, 154b, and 154c.

The flexible substrate 54 and the holder 56 according to this embodiment are formed so that the flexible substrate 54 is easily positioned relative to the holder 56 and so that the flexible substrate 54 can be easily affixed to the holder 56. Thus, according to the operation section 12 and the endoscope 10 including the operation section 12 in this embodiment, it is possible to reduce number of assemble processes while also improving assembly workability.

It is possible to regulate the movement of the first key attachment portion 124a of the flexible substrate 54 relative to the first attachment surface 152 in the longitudinal direction L2 by engaging the first engagement protrusions 186a and 186b of the first attachment surface 152 with the first engagement recesses 126a and 126b of the flexible substrate 54. Thus, detachment of the first key attachment portion 124a from the first attachment surface 152 can be difficult even if force is continuously applied to detach the first key attachment portion 124a of the flexible substrate 54 from the first attachment surface 152.

It is also possible to regulate the movement of the second key attachment portion 124b of the flexible substrate 54 relative to the second attachment surface 154 in the longitudinal direction L2 by engaging the second engagement protrusions 188a and 188b of the second attachment surface 154 with the second engagement recesses 128a and 128b of the flexible substrate 54. Thus, detachment of the second key attachment portion 124b from the second attachment surface 154 can be difficult even if force is continuously applied to detach the second key attachment portion 124b of the flexible substrate 54 from the second attachment surface 154.

Furthermore, even if the press body 74a is pressed during the use of the endoscope 10, the first key attachment portion 124a of the flexible substrate 54 is fixed to the first attachment surface 152 by the adhesive agent, and the engagement protrusions 186a and 186b are engaged with the first engagement recesses 126a and 126b. Even if the press bodies 76a, 76b, and 76c are suitably pressed during the use of the endoscope 10, the second key attachment portion 124b of the flexible substrate 54 is fixed to the second attachment surface 154 by the adhesive agent, and the engagement protrusions 188a and 188b are engaged with the engagement recesses 128a and 128b. It is therefore possible to effectively prevent the displacement of the flexible substrate 54 relative to the holder 56.

The engagement protrusions 186a and 186b are separated relative to the longitudinal direction L3 in the width direction in the first attachment surface 152 in particular. It is therefore possible to resist twisting when the first key attachment portion 124a is twisted during or after the attachment of the first key attachment portion 124a to the first attachment surface 152.

In the second attachment surface 154, the engagement protrusions 188a and 188b are separated along the longitudinal direction L3. This can prevent the displacement of the second key attachment portion 124b of the flexible substrate 54 along the longitudinal direction L2 thereof relative to the longitudinal direction L3 of the second attachment surface 154.

The cavity portion 138 is formed not only by communicating the first and second openings 134 and 136 but also by communicating the third and fourth openings 172 and 174. In this instance, the space of the cavity portion 138 is formed by use of not only one of the third and fourth openings 172 and 174 but also both of the third and fourth openings 172 and 174. Especially, the third and fourth openings 172 and 174 do not reach the opposite side surface. Thus, the opening amounts of the third and fourth openings 172 and 174 can be smaller than when the third and fourth openings 172 and 174 pierce from one side surface 146 to the other side surface 148 with the same shape. It is therefore possible to maintain suitable strength in the vicinity of the top 150 of the body 132 of the holder 56.

In the example described here, the flexible substrate 54 is guided into the cavity portion 138 from the outside of the body 132 through the second opening 136, and the flexible substrate 54 is guided to the outside of the body 132 from the inside of the cavity portion 138 through the first opening 134. Alternatively, the flexible substrate 54 may be guided into the cavity portion 138 from the outside of the body 132 through the first opening 134, and the flexible substrate 54 may be guided to the outside of the body 132 from the inside of the cavity portion 138 through the second opening 136.

Although it has been described here that the second belt-shaped portion 122b of the flexible substrate 54 is smaller in width than the first and second key attachment portions 124a and 124b, the width may be the same if the second belt-shaped portion 122b can be bent. Although it has been described that the first and second key attachment portions 124a and 124b are displaced in the width direction that intersects at right angles with the longitudinal direction L2, the first and second key attachment portions 124a and 124b do not always need to be displaced.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscopic operation section to operate an endoscope, the endoscopic operation section comprising:
    an elastically deformable belt-shaped flexible substrate which is disposed inside the endoscopic operation section and which has a switch function; and
    a holder which is disposed inside the endoscopic operation section and which fixes the flexible substrate, the holder including:
        a top formed in the outer circumference of the holder,
        a first opening to pass the flexible substrate into the holder from the outside of the holder,
        a second opening to pass the flexible substrate to the outside of the holder from the inside of the holder, the second opening being provided so that the top is provided between the first opening and the second opening in the outer circumference of the holder,
        a cavity portion formed inside the holder to communicate the first opening and the second opening,
        a first attachment surface to which the flexible substrate is attached, the first attachment surface being adjacent to the first opening on the opposite side of the first opening from the top in the outer circumference of the holder, and
        a second attachment surface which is adjacent to the second opening on the opposite side of the second opening from the top; wherein:
    the cavity portion is defined by a ceiling portion and a bottom surface portion which is spaced from the ceiling portion and which faces the ceiling portion, and
    the belt-shaped flexible substrate is loosely provided between the ceiling portion and the bottom surface portion without contacting the ceiling portion and the bottom surface portion when the holder fixes the belt-shaped flexible substrate.

2. The endoscopic operation section according to claim 1, further comprising an operation section main body which forms an outer shell of the endoscopic operation section, the elastically deformable belt-shaped flexible substrate and holder being housed within the operation section main body.

3. The endoscopic operation section according to claim 2, wherein:
    the flexible substrate includes:
    a first key attachment portion in which a first key portion that is operated by pressing from the outside of the operation section main body is provided and which is attached to the first attachment surface,
    a second key attachment portion in which a second key portion that is operated by pressing from the outside of the operation section main body is provided and which is attached to the second attachment surface, and
    a flexible belt-shaped portion provided between the first and second key attachment portions, and
    the belt-shaped portion is configured to be deformed so that the first and second key attachment portions substantially face each other.

4. The endoscopic operation section according to claim 3, wherein:
    the holder includes first and second side surfaces which are adjacent to the first and second attachment surfaces and which are separate from each other, and
    the top is provided between the first and second side surfaces.

5. The endoscopic operation section according to claim 4, wherein:
    a third opening which communicates with the cavity portion is formed in the first side surface, and
    a fourth opening which communicates with the cavity portion and which is continuous with the ceiling portion is formed in the second side surface.

6. The endoscopic operation section according to claim 5, wherein:
    the first key attachment portion, the belt-shaped portion, and the second key attachment portion of the flexible substrate are provided along a longitudinal direction of the flexible substrate, and
    a space between a distal end distally-positioned from the third opening toward the second side surface and a distal end distally-positioned from the fourth opening toward the first side surface has a width greater than a width of the belt-shaped portion that intersects at right angles with the longitudinal direction.

7. The endoscopic operation section according to claim 3, wherein:
    the first key attachment portion, the belt-shaped portion, and the second key attachment portion of the flexible substrate are provided along a longitudinal direction of the flexible substrate, and
    the ceiling portion has a width greater than a width of the belt-shaped portion that intersects at right angles with the longitudinal direction.

8. The endoscopic operation section according to claim 3, wherein the cavity portion houses the belt-shaped portion.

9. The endoscopic operation section according to claim 3, wherein:
    the cavity portion includes:
    a guide portion which guides the flexible substrate into the cavity portion from the outside of the holder through one of the first and second openings and which guides the flexible substrate to the outside of the holder from the inside of the cavity portion through the other of the first and second openings, and
    a housing portion located adjacent to the guide portion that houses the belt-shaped portion in a state where the belt-shaped portion is bent between the bottom surface portion and the ceiling portion when the first key attachment portion is attached to the first attachment surface and the second key attachment portion is attached to the second attachment surface.

10. The endoscopic operation section according to claim 3, wherein:
    the second key portion has key bodies provided in the second key attachment portion of the flexible substrate,
    the second attachment surface has at least one bent portion,
    the second key attachment portion of the flexible substrate has an abutment portion which abuts on the bent portion, and
    the flexible substrate includes, in a surface of the second key attachment portion opposite to a surface to which the second key portion is attached, a coated portion which is coated with an adhesive agent to the second attachment surface, an uncoated portion which is not coated in a part corresponding to the abutment portion, and a mold release sheet which integrally covers the coated portion and the uncoated portion and which is configured to be released from the coated portion.

11. The endoscopic operation section according to claim 3, wherein:
the first key attachment portion, the belt-shaped portion, and the second key attachment portion of the flexible substrate are provided along a longitudinal direction of the flexible substrate, and
the first attachment surface has a first engagement portion which is configured to engage with the first key attachment portion of the flexible substrate and which regulates the movement of the flexible substrate in the longitudinal direction.

12. The endoscopic operation section according to claim 3, wherein:
the first key attachment portion, the belt-shaped portion, and the second key attachment portion of the flexible substrate are provided along a longitudinal direction of the flexible substrate, and
the second attachment surface has a second engagement portion which is configured to engage with the second key attachment portion of the flexible substrate and which regulates the movement of the flexible substrate in the longitudinal direction.

13. The endoscopic operation section according to claim 1, wherein:
the first attachment surface has, at an end separate from the top, a first passage which guides the flexible substrate into the holder, and
the second attachment surface has, at an end separate from the top, a second passage which guides the flexible substrate into the holder.

14. An endoscope comprising:
the operation section according to claim 1;
an insertion section coupled to the operation section;
an illumination optical system provided inside the operation section and the insertion section; and
an observation optical system which is provided inside the operation section and the insertion section and which is provided in parallel with the illumination optical system.

* * * * *